United States Patent
Kadhiresan

[11] Patent Number: 5,974,340
[45] Date of Patent: Oct. 26, 1999

[54] APPARATUS AND METHOD FOR MONITORING RESPIRATORY FUNCTION IN HEART FAILURE PATIENTS TO DETERMINE EFFICACY OF THERAPY

[75] Inventor: V. A. Kadhiresan, Lino Lakes, Minn.

[73] Assignee: Cardiac Pacemakers, Inc., St. Paul, Minn.

[21] Appl. No.: 08/840,425

[22] Filed: Apr. 29, 1997

[51] Int. Cl.⁶ .................................................. A61N 1/365
[52] U.S. Cl. .................................................................. 607/18
[58] Field of Search .................................. 607/18, 19, 20

[56] References Cited

U.S. PATENT DOCUMENTS

| | | | |
|---|---|---|---|
| 5,063,927 | 11/1991 | Webb et al. | 607/19 |
| 5,137,119 | 8/1992 | Pederson et al. | 607/20 |
| 5,300,092 | 4/1994 | Schaldach | 607/19 |
| 5,355,894 | 10/1994 | Sivard | 607/20 |

*Primary Examiner*—William E. Kamm
*Attorney, Agent, or Firm*—Nikolai, Mersereau & Dietz, P.A.

[57] ABSTRACT

The respiratory function of a patient is measured for diagnostic purposes using a cardiac rhythm management device. Monitoring of the respiratory activity is initiated after a microprocessor in the cardiac rhythm management device determines that the patient has been at rest for a predetermined length of time. A respiration related signal is derived from either an accelerometer signal or from an impedance sensor, depending upon which produces a signal has the higher signal-to-noise ratio. The signal from either the accelerometer or impedance measuring mechanism is low-pass filtered to obtain a respiratory signal component. The respiratory signal component is digitized and sent to the microprocessor for analysis. The microprocessor can be programmed in either of two modes of analysis. In the first mode, the peak-to-peak values of the respiratory signal component over a number of fixed time interval is summed, obtaining the minute volume. In the second method, the entire waveform history during the fixed time interval is stored in the microprocessor. The stored information is then telemetered out to the physician when interrogated. The physician may then review the information and then determines the efficacy of a treatment regimen administered to the patient.

12 Claims, 4 Drawing Sheets

APPARATUS AND METHOD FOR MONITORING RESPIRATORY FUNCTION IN HEART FAILURE PATIENTS TO DETERMINE EFFICACY OF THERAPY

I. FIELD OF THE INVENTION

This invention relates generally to an implantable, programmable cardiac stimulating apparatus including means for monitoring the respiratory function of a patient.

II. DISCUSSION OF THE PRIOR ART

Congestive heart failure (CHF) patients suffer from respiratory discomfort or shortness of breath. Fluids accumulate in the interstitial tissues of the lungs of CHF patients due to high ventricular filling pressure. The CHF patient experiences respiratory disfunction due to the lung congestion. A commonly observed symptom is shortness of breath which is aggravated when the CHF patient is lying in bed. In addition, CHF patients often experience breathing characterized by rhythmic waxing and waning of the depth of respiration with regularly recurring periods of apnea, clinically described as Cheyne-stokes breathing.

There are two kinds of sleep apnea and both are associated with heart disease. Central sleep apnea is the most common type found and is probably caused by heart failure. This type of apnea may be developed after a heart attack and is usually a contributing factor to heart failure. During central sleep apnea, patients stop breathing and begin to suffocate causing them to wake-up. The awakening jolts their heart muscles into action when they should be resting and thus the jolting action puts stress on the heart.

The other type of apnea is obstructive sleep apnea and may contribute to heart failure. Obstructive sleep apnea is commonly found in overweight people who snore and have oversized necks. Muscle tone keeps the throat open during the day, but at night the weight of the oversized neck narrows the airway. As a result, the tongue falls back closing the airway. The person struggles to breath against the collapsed throat as if choking. This breathing effort puts an additional strain on the heart. Patients with congestive heart failure of unknown origin frequently suffer from obstructive sleep apnea.

Cardiovascular disease is worsened by excessive pressure the heart undergoes during the intermittent periods of apnea. According to researchers at the Cardiorespiratory Sleep Disorder Clinic at the Toronto Hospital, Toronto, Canada, approximately 40% of heart failure patients have sleep apnea compared to 6% of non-heart failure population. Patients may have undiagnosed sleep apnea which may be more appropriately treated with continuous positive airway pressure. Instead of using expensive medications, such treatment strengthens the respiratory muscle (the diaphragm) which reduces shortness of breath, a main symptom of heart failure.

A CHF patient's quality of life depends to a large degree upon the respiratory function. Upon administration of the appropriate therapy, respiratory function is improved and patient discomfort eases. Non-invasive therapy to relieve lung congestion can be short term and long term. Intervention for this condition ranges from conventional drug therapy to new therapies under evaluation, such as pacing. With therapy, the patient improves and the respiratory rate decreases with a concomitant increases in tidal volume.

Cardiac rhythm management devices already measure activity and respiratory signals for the purposes of rate adaptive pacing. Respiration can be determined by minute ventilation which is the product of respiratory rate and tidal volume. Minute ventilation is estimated by frequent measurements of transthoracic impedance between an intracardiac lead and the pulse generator case using a bipolar system. A low energy pulse of known current amplitude, well below the threshold of stimulation, is delivered from the ring electrode of a standard bipolar pacing lead. The resultant voltage between the tip electrode and the pulse generator case is measured and the impedance is calculated. By measuring the frequency of respiration, related fluctuations in impedance (correlated with respiratory rate) and the amplitude of those excursions (correlated with tidal volume) minute ventilation can be estimated. The respiratory information derived from the impedance waveform can be used as a physiological functional parameter for determining optimum pacing rate in a rate responsive pacer or can be used to monitor respiratory activity.

The transthoracic impedance signal is a complex parameter influenced by several factors. However, the transthoracic impedance is most closely related to the volume and resistivity of the blood in the heart and the systemic venous system. The impedance signal fluctuates in response to both respiration and cardiac motion (ventricular ejection). In order to minimize the cardiac-related component of the impedance signal, low pass filtering is performed.

Another type of activity sensing pacemakers uses body vibration during physical activity as an indication of the need to alter pacing rate. The body vibration can be sensed by either motion sensors or accelerometers located inside the pulse generator case. The band width of the accelerometer signal for sensing activity ranges from 1 Hz to 10 Hz.

The present invention is an implantable device used to monitor the respiratory function and to provide the monitored information to the physicians for optimizing therapy for the patient. The apparatus and method includes a means for monitoring the respiratory function of the patient by using either an impedance signal or an accelerometer in an implanted cardiac rhythm management device. An accelerometer signal with a band width of about 0.05–140 Hz can clearly represent frequency and amplitude of the chest wall movement. By monitoring respiratory rate, an approximate tidal volume can be inferred. The present invention is a diagnostic device which either counts a number of respiratory episodes or saves the entire respiratory history. Once the data is collected, it can be telemetered out for the physician review. The physician is then able to optimize the pacing or drug therapy for the patient.

It is accordingly a principal object of the present invention to provide a dual function implantable cardiac rhythm management device having the capability to monitor respiratory function as a diagnostic tool, store the monitored respiratory information and then the monitored information can subsequently be used to optimize therapy for CHF patient, particularly a CHF patient.

Another object of the present invention is to provide an implantable device that utilizes an accelerometer to monitor chest wall movement and from which the respiratory function of a patient can be derived, that stores the monitored information and that allows retrieval of the information from which an optimal therapy can be determined and implemented.

A further object of the present invention is to selectively utilize an impedance measurement of respiration or an accelerometer measurement of respiration for monitoring a patient's respiratory function to optimize therapy.

SUMMARY OF THE INVENTION

The present invention measures the respiratory function of the patient for diagnostic purposes with a conventional rate responsive pacer located either in the left or right pectoral region. The monitoring of the respiratory activity is initiated only after a microprocessor in the pacer determines that the patient has been at rest for a predetermined length of time. The respiration signal is derived from either an accelerometer signal or by impedance plethysmography, depending upon which signal has the better signal-to-noise ratio.

If the microprocessor determines that the accelerometer signal affords the better signal-to-noise ratio, the accelerometer signal is low pass-filtered by a filter having a band width of about 0.05–2 Hz to obtain the respiratory signal component of the sensed waveform.

If the microprocessor determines that an impedance measurement has the better signal-to-noise ratio, intracardiac impedance signals are obtained. This signal is then low pass filtered at around a 2 Hz cut off frequency to isolate the ventilation activity component. The respiration signal component obtained from either the accelerometer or impedance is digitized and sent to the microprocessor for analysis.

The microprocessor can be programmed to operate in either one of two methods of analysis. In the first method, the peak-to-peak value of the signal over a fixed time interval is summed, obtaining a signal proportional to the minute volume. The number of fixed time intervals is counted and the count is stored. In the second method, the entire waveform history of the fixed time interval is stored in memory as directed by the microprocessor.

The stored information is then available to be telemetered out to the physician. The physician may then review the information and then determine the optimum treatment for the patient.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which.

DETAILED DESCRIPTION OF THE PREFERRED EMBODIMENT

Figure 1:
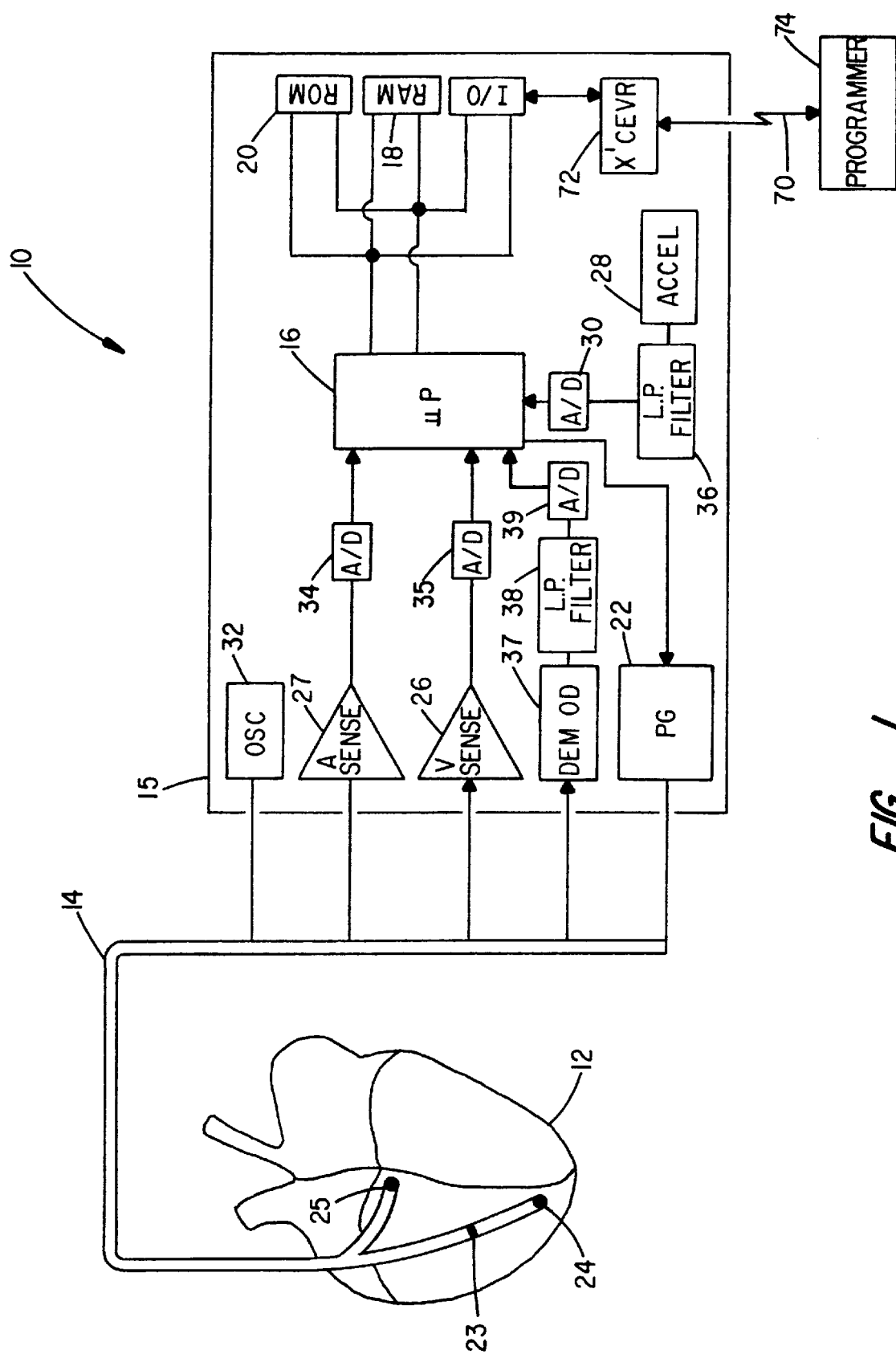
FIG. 1 is a block diagram of a cardiac rhythm management device used with the present invention.

The present invention is implemented in a cardiac rhythm management device, shown generally by the schematic block diagram of FIG. 1. The cardiac rhythm management device 10 is operatively connected to a patient's heart 12 by electrical conductors embodied in a pacing lead 14. The housing or casing 15 of the cardiac rhythm management device is implanted in a surgically made pocket, typically in either the left or right pectoral region of the patient. The cardiac rhythm management device 10 includes microprocessor-base controller 16 that is programmed to operate in a plurality of modes, well known to those skilled in the art. The microprocessor has a RAM (random access memory) 18 and ROM (read only memory) 20 for storing programs and data. The microprocessor 16 controls the delivery of cardiac stimulation pulses by a pulse generator 22 to the simulating electrodes 24 and 25 on the pacing lead 14. The electrode 24 is connected to a ventricular sense amplifier 26 and the electrode 25 is connected to the atrial sense amplifier 27. They are arranged to sense the atrial and ventricle depolarization events depending upon the programmed mode of the cardiac rhythm management device 10 being utilized (DDD, VVI, etc). The signal representing the sensed activity is fed to an analog-to-digital converter 34 and 35 and then the digitized signal is fed to the input of the microprocessor-based controller 16 for evaluation and for determining cardiac stimulation.

In accordance with the present invention, an accelerometer 28 may be positioned within the casing or housing 15 of the cardiac rhythm management device 10 and coupled to the microprocessor-based controller 16 through an analog to digital converter 30. By positioning the accelerometer 28 in the casing, the accelerometer 28 generates a global signal associated with the various atrial and ventricular events. Alternatively, an accelerometer (not shown) attached to the lead to sense the atrial and ventricular events more locally may be used. A localized signal tends to be more free of noise. If the implantable device 10 is to be used to measure intracardiac impedance, an oscillator 32 will be incorporated within the case for applying a high frequency carrier between electrodes 23 and 24 in the right ventricle or between the metal case 15 and electrode 24.

Figure 3:
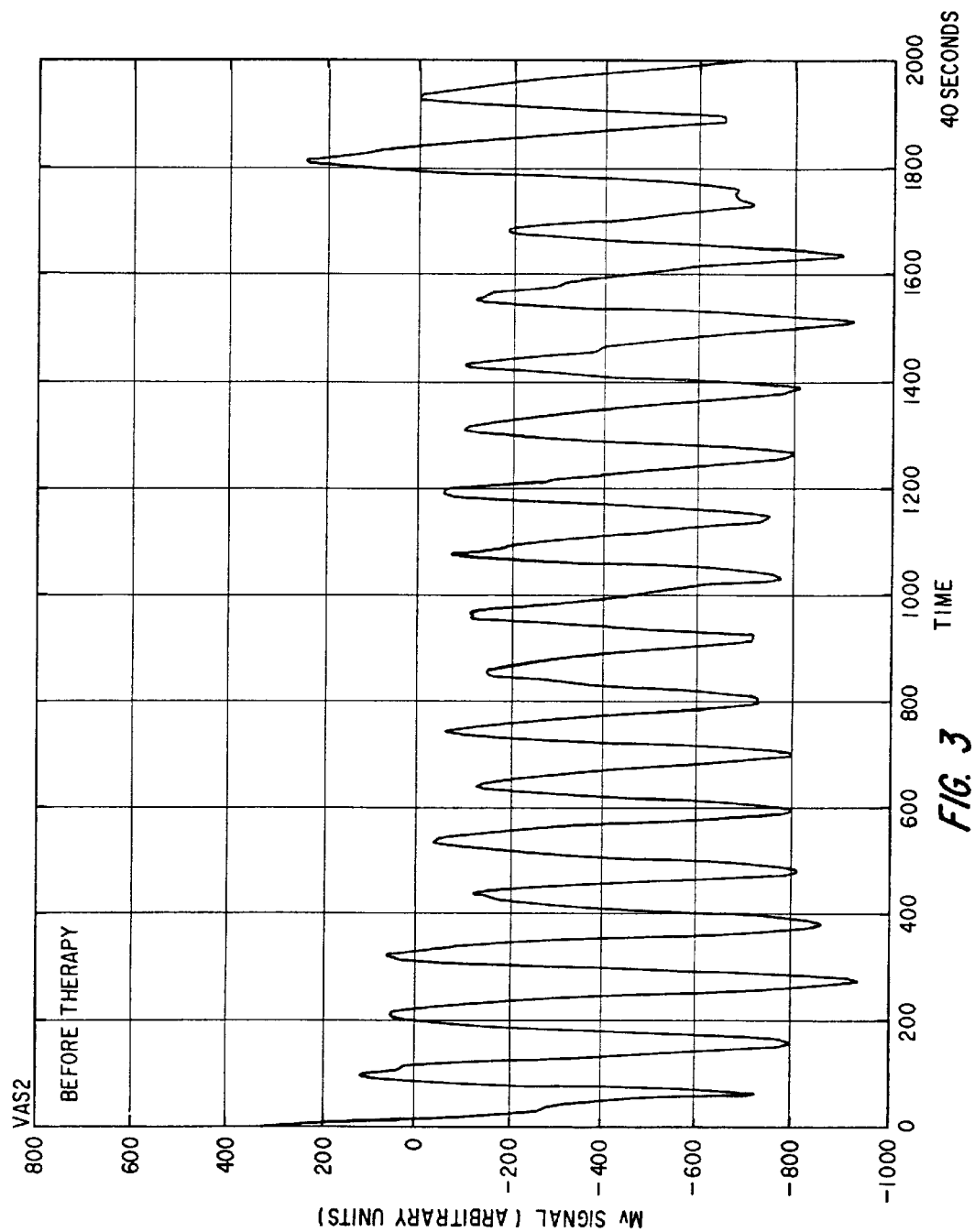
FIG. 3 is a diagram of a representative waveform respiratory function derived from an accelerometer signal.

The analog signal output of the accelerometer 28 comprises events associated with the heart sounds, compressions, cardiac wall accelerations and decelerations caused by cardiac events along with motion artifacts and respiratory events. The signal is low pass filtered, preferably with a 2 Hz cut-off frequency, with filter 36 to obtain the respiratory signal. In this particular case, the resultant waveform is associated with respiration or minute volume, and one such wave form is shown in FIG. 3. The accelerometer signal is transmitted to an analog to digital converter 30 where it is digitized before being transmitted to the microprocessor 16. At the microprocessor 16, the digitalized signal is signal processed and analyzed. While a discrete analog low pass filter 36 is shown in FIG. 1, digital filtering can also be done in the digital domain within the microprocessor based controller.

Respiration may also be delivered and monitored from the intracardiac impedance measurements. As well known, the oscillator 32 is used to provide a relatively high frequency, low amplitude alternating current for impedance measurement. A carrier frequency typically between 1 kHz and 100 kHz may be used. The respiratory or pulmonary and cardiac signals modulate the carrier and are readily separated from the high frequency carrier by a demodulator 37. The intracardiac impedance measurements are generally low-pass filtered with filter 38 to isolate the ventilation activity where amplitude is related to tidal volume. More particularly, this signal may be low-pass filtered at about a 2 Hz cut off frequency to isolate the ventilation activity component.

Figure 4:
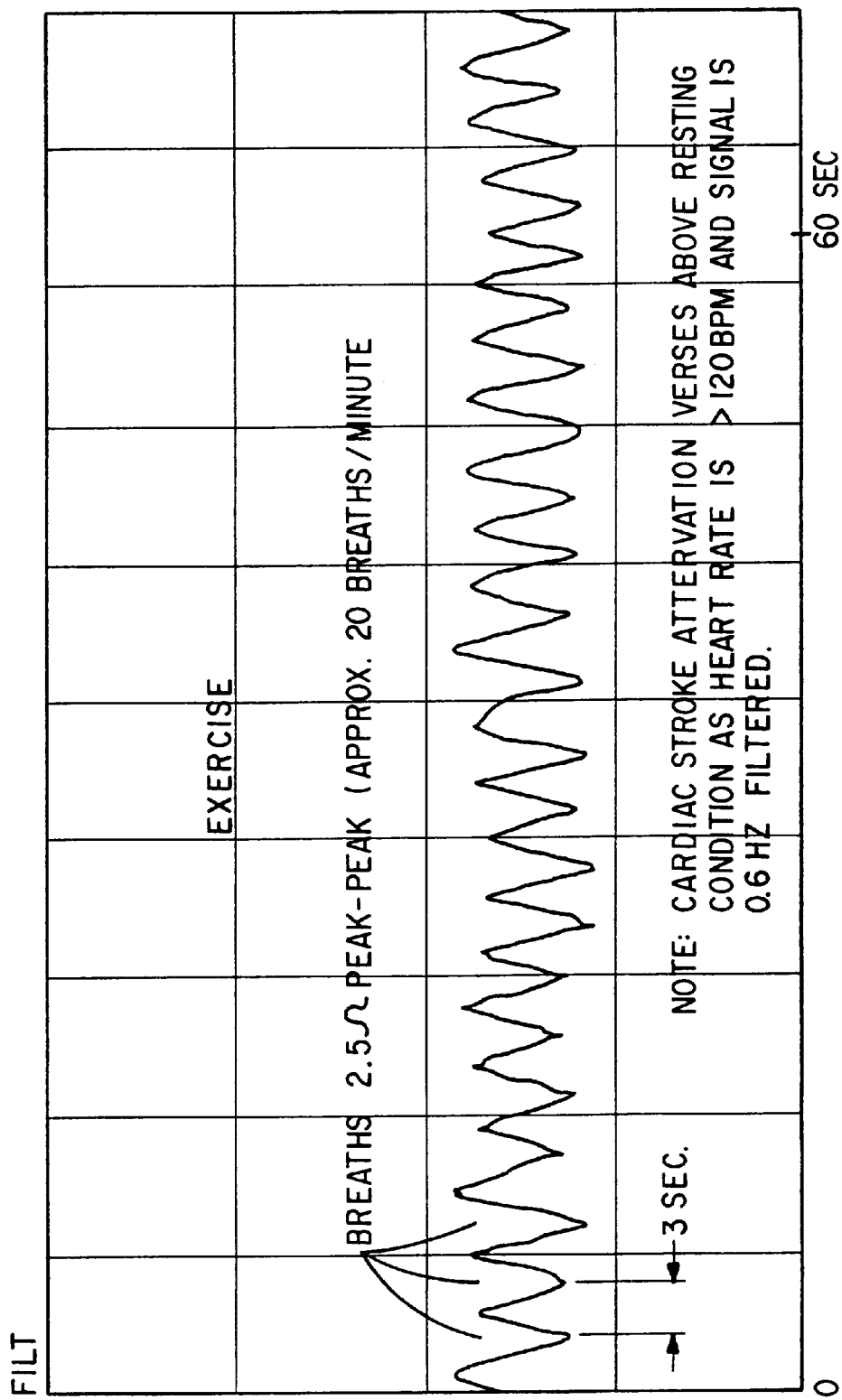
FIG. 4 is a diagram of a representative waveform respiratory function obtained from impedance measurement.

FIG. 4 contains a typical waveform showing the ventilation activity. The filter outputs are sent to the analog to digital converter 39. The resulting digitalized signal is proportional to the associated respiratory rate as well as the depth of respiration. While the block diagram shows four separate A/D converters 30, 34, 35 and 39, a single converter may be time shared.

Figure 2:
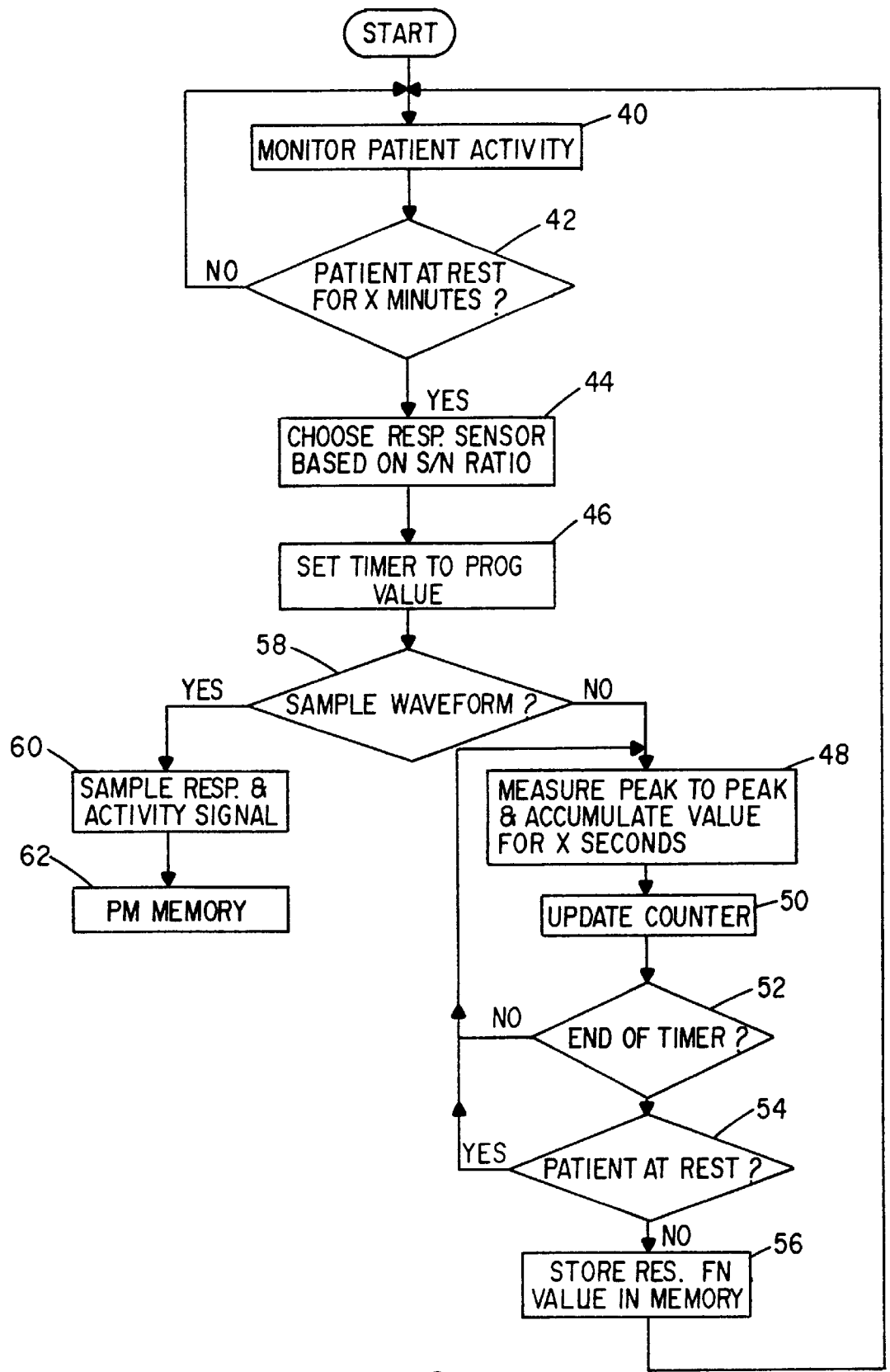
FIG. 2 is a block diagram of a software flow chart for the algorithm incorporating the steps of the present invention.

The microprocessor 16 is programmed with certain parameters which include an activity level threshold, a period of quiet time, a total time to observe respiratory signals, a bin size for collecting respiratory signals and a maximum number of bins. The microprocessor is programmed to monitor respiratory function and to follow the steps outlined in the flow diagram of FIG. 2. The patient activity as determined by the accelerometer, is monitored (block 40) to determine when the patient is at rest. When it is determined that the patient is at rest for a predetermined programmed time interval (block 42), the microprocessor 16 chooses either the accelerometer or impedance respiratory sensor, based on a determination of which affords the better S/N ratio (block 44). The microprocessor then sets an internal timer to a programmed value for the total time in which to observe the respiratory signals (block 46).

The microprocessor 16 can be programmed in one of two ways to sample the respiratory activity. In the first mode, the microprocessor 16 receives the digitized signal representing respiration and measures the waveforms peak-to-peak excursions and accumulates the values for a predetermined number of seconds (block 48). A counter is then updated (block 50). If the predetermined amount of time is still running (block 52), control returns to block 48 and continues to measure the waveforms peak-to-peak excursions, accumulating the values for the predetermined number of seconds. Steps 48–52 are repeated until the timer has reached a predetermined count. The microprocessor then determines if the patient is still at rest (block 54). If the patient is still at rest, the microprocessor returns to block 48 and measures peak-to-peak values of the waveform in predetermined time intervals and accumulates their values for the predetermined number of seconds. Steps 48–54 continue until the patient is no longer at rest. At this time, the measured respiratory function value is stored in the memory (block 56).

In a second mode, a decision is made (block 58) to sample the actual waveform of the respiratory and activity signal. The waveform is obtained over the entire programmed time (block 60). The entire waveform is then stored in the RAM (block 62).

Once stored, the respiratory information can then later be telemetered out to the external programmer for display and analysis. The device is preferably capable of telemetering various status information in a conventional way through a telemetry link 70 including a transceiver 72 and an external programmer 74. The external programmer 74 transmits information back to the implant to interrogate and to reprogram various parameters. Based on the information provided by the monitored and stored respiratory function, the administered therapies can be adjusted appropriately.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac rhythm management device having means for sensing events of a patient's cardiac activity and means for applying stimulating pulses to the patient's heart at timed intervals, the device including an impedance measurement means for producing a signal representative of intracardiac volume and an accelerometer for producing a signal representative of patient activity and mechanical movement of cardiac tissue of said patient, said cardiac rhythm management device comprising:

a) first signal processing means coupled to said impedance measurement means for producing a first signal component representative of minute volume of said patient over a predetermined number of respiratory cycles;

b) second signal processing means coupled to said accelerometer for producing a second signal component representative of said patient's mechanical movement events due to respiration; and c) a controller having a programmed microprocessor coupled to said first and second signal processing means and having timing means, means for receiving said first and second signal components, means for selectively analyzing the first and second signal components over said predetermined number of respiratory cycles during a predetermined time interval defined by said timing means, and means for storing a selected one of the first and second signal components for subsequent retrieval and analysis.

2. A cardiac rhythm management device of claim 1 and further including telemetering means for transmitting said stored first and second signal components and an external device for receiving the first and second signal components.

3. A cardiac rhythm management device of claim 1 wherein said means for selectively analyzing further includes means for evaluating signal-to-noise ratio of said first and second signal components and means for selecting a one of the first and second signal components having the greater signal-to-noise ratio as the signal component stored by the storing means.

4. A cardiac rhythm management device of claim 3 wherein said controller further includes means for determining whether said patient is at rest and means responsive to the at rest determining means for inhibiting the signal-to-noise ratio evaluating means until an at rest state condition is satisfied.

5. A cardiac rhythm management device for a patient's heart, said cardiac rhythm management system comprising:

a) means for sensing cardiac depolarization events and producing a first signal representative thereof;

(b) means for applying cardiac stimulating signals to the heart;

(c) impedance measuring means for generating a second signal representative of intracardiac impedance, including components correlating with events of respiration of the patient;

(d) an accelerometer for generating a third signal including components correlating with mechanical events of the patient's respiration; and (e) a controller having a microprocessor coupled to said sensing means, said accelerometer and said impedance measurement means, said controller having means for determining from the third signal when said patient is at rest, means for initiating an analysis of said second and third signals only when the patient is at rest, analyzing means for selectively analyzing one of said second and third signals over a predetermined time interval while said patient is at rest, means for storing said analyzed signal, and means responsive to said first signal and at least one of the second and third signals for controlling said means for applying cardiac signals to the heart.

6. A cardiac rhythm management device of claim 5 and further including telemetering means for transmitting said stored analyzed signal, and an external device for receiving the analyzed signals.

7. A cardiac rhythm management device of claim 5 wherein said analyzing means for selectively analyzing further includes means for evaluating signal-to-noise ratio of said first and second signals and selecting for analysis the one of said first and second signals with a higher signal-to-noise ratio.

8. A method for monitoring respiratory function of a patient comprising the steps of:

a) implanting a cardiac rhythm management device within a patient, the cardiac rhythm management device having a controller with a microprocessor, a memory, a means for measuring intracardiac impedance and an accelerometer for sensing mechanical events relating to respiratory activity of the patient, a means for sensing cardiac depolarization events and a means for applying cardiac stimulating pulses to the patient's heart;

b) receiving a first signal from the accelerometer;

c) receiving a second signal from the means for measuring intracardiac impedance;

d) determining from the first signal if said patient is a rest;

e) evaluating said first and second signals to determine a signal-to-noise ratio for said first and second signals when said patient is at rest;

f) selecting the one of the first and second signals having the higher signal-to-noise ratio;

g) setting a predetermined time interval;

h) filtering said selected signal to obtain a portion of the selected signal corresponding to respiratory activity of said patient;

i) measuring said selected signal for said predetermined time interval;

j) storing said measured selected signal in said memory of said controller; and k) repeating steps b–j until patient is no longer at rest.

9. A method of claim 8 and further comprising the steps of: telemetering said stored signal.

10. A method of claim 8 and further comprising the step of storing the waveform of the selected signal of each time interval while said patient is at rest for subsequent retrieval and analysis.

11. A method for monitoring respiratory function of a patient comprising the steps of:

a) implanting in such patient a cardiac rhythm management device having means for sensing cardiac depolarization events, means for applying electrical stimulation signals to the patient, an accelerometer for sensing mechanical respiration events, an impedance measuring means for sensing intracardiac impedance and a controller with a programmed microprocessor having a memory, the microprocessor receiving a first signal corresponding to said cardiac depolarization events, a second signal corresponding to mechanical respiration events and a third signal corresponding to intracardiac impedance;

b) determining from the second signal whether the patient is at rest;

c) evaluating said second and third signals when said patient is at rest; to determine a signal-to-noise ratio for said second and third signals;

d) selecting the one of the second and third signals with the greater signal-to-noise ratio;

e) filtering said selected signal to obtain a component of said selected signal corresponding to respiratory activity of said patient;

f) measuring peak-to-peak values of said selected signal over a predetermined time interval;

g) summing measured peak-to-peak values;

h) storing said summed peak-to-peak values in said memory of said microprocessor for subsequent retrieval and analysis;

i) repeating steps b–h until patient is no longer at rest; and j) updating a counter for each iteration of steps b–h.

12. A method of claim 11 and further comprising the step of telemetering the stored signals.

* * * * *